US012263637B2

(12) United States Patent
Seitz et al.

(10) Patent No.: US 12,263,637 B2
(45) Date of Patent: Apr. 1, 2025

(54) METHOD FOR PRODUCING 3D-PRINTED ACTIVE SUBSTANCE-RELEASING SYSTEMS WITH ACTIVE SUBSTANCE DEPOTS

(71) Applicant: UNIVERSITÄT ROSTOCK, Rostock (DE)

(72) Inventors: Hermann Seitz, Rostock (DE); Roland Matzmohr, Neuendorf (DE); Niels Grabow, Rostock (DE); Michael Teske, Rostock (DE); Thomas Eickner, Rostock (DE); Robert Mau, Rostock (DE); Alexander Riess, Rostock (DE); Klaus-Peter Schmitz, Rostock (DE)

(73) Assignee: Universitaet Rostock, Rostock (DE)

( * ) Notice: Subject to any disclaimer, the term of this patent is extended or adjusted under 35 U.S.C. 154(b) by 0 days.

(21) Appl. No.: 17/037,099

(22) Filed: Sep. 29, 2020

(65) Prior Publication Data

US 2021/0078248 A1 Mar. 18, 2021

Related U.S. Application Data

(63) Continuation of application No. PCT/EP2019/057734, filed on Mar. 27, 2019.

(30) Foreign Application Priority Data

Mar. 29, 2018 (DE) ...................... 10 2018 107 585.5

(51) Int. Cl.
*B29C 64/209* (2017.01)
*A61K 9/00* (2006.01)
(Continued)

(52) U.S. Cl.
CPC .......... *B29C 64/209* (2017.08); *A61K 9/0024* (2013.01); *B29C 64/112* (2017.08);
(Continued)

(58) Field of Classification Search
CPC ... B29C 64/209; B29C 64/112; B29C 64/124; B29C 64/194; A61K 9/0024;
(Continued)

(56) References Cited

U.S. PATENT DOCUMENTS 2,082,226 A * 6/1937 Stafford .................. E03C 1/108
137/216
3,774,197 A * 11/1973 Meek ............... H03K 19/09441
341/64

(Continued)

FOREIGN PATENT DOCUMENTS

CN 105643936 A * 6/2016
CN 205818475 U 12/2016
(Continued)

OTHER PUBLICATIONS

CN 105643936 translation (Year: 2023).*
(Continued)

*Primary Examiner* — Jeffrey M Wollschlager
*Assistant Examiner* — Guy F Mongelli
(74) *Attorney, Agent, or Firm* — Muncy, Geissler, Olds & Lowe, P.C.

(57) ABSTRACT

A device for producing a 3D-printed active substance-releasing system with active substance depots, such that a radiation source in operation causes a polymerisation of a layer of the base material on the construction platform and that an inkjet printhead incorporates an active substance mixture, which has at least one active substance, into the base material in a locationally selective manner. A trough is provided, in which a base material and a construction platform are arranged, and polymerising selected regions of a layer of the base material on the construction platform and introducing, by means of an inkjet printing method, an active substance mixture, which has at least one active (Continued)

substance, into the base material and/or polymerised base material in a locationally selective manner in order to thereby create active ingredient depots in the active ingredient-releasing system.

13 Claims, 2 Drawing Sheets

(51) Int. Cl.
| | | |
|---|---|---|
| B29C 64/112 | (2017.01) | |
| B29C 64/124 | (2017.01) | |
| B29K 105/00 | (2006.01) | |
| B33Y 10/00 | (2015.01) | |
| B33Y 30/00 | (2015.01) | |
| B33Y 70/00 | (2020.01) | |
| B33Y 80/00 | (2015.01) | |
| C09D 11/101 | (2014.01) | |
| C09D 11/38 | (2014.01) | |

(52) U.S. Cl.
CPC ............ *B29C 64/124* (2017.08); *B33Y 10/00* (2014.12); *B33Y 30/00* (2014.12); *B33Y 70/00* (2014.12); *C09D 11/101* (2013.01); *C09D 11/38* (2013.01); *B29K 2105/0002* (2013.01); *B33Y 80/00* (2014.12)

(58) Field of Classification Search
CPC ...... A61K 9/2095; B33Y 10/00; B33Y 30/00; B33Y 70/00; B33Y 80/00; C09D 11/101; C09D 11/38; B29K 2105/0002; A61L 27/16; A61L 27/54
See application file for complete search history.

(56) References Cited

U.S. PATENT DOCUMENTS

| | | | | |
|---|---|---|---|---|
| 5,490,962 A * | 2/1996 | Cima | ............... | A61K 9/1647 264/41 |
| 6,176,874 B1* | 1/2001 | Vacanti | ............... | A61L 27/3808 623/901 |
| 6,821,473 B2 | 11/2004 | Hiizumi et al. | | |
| 7,077,334 B2* | 7/2006 | Sachs | ............... | B41J 2/1429 239/11 |
| 7,250,759 B2* | 7/2007 | Kahlman | ............... | G01R 33/12 324/252 |
| 9,381,154 B2 | 7/2016 | Zhou et al. | | |
| 2001/0029983 A1* | 10/2001 | Unger | ............... | F16K 99/0046 428/188 |
| 2001/0042942 A1 | 11/2001 | Hizumi et al. | | |
| 2002/0015728 A1* | 2/2002 | Payumo | ............... | A61P 43/00 424/451 |
| 2003/0133975 A1* | 7/2003 | Yoo | ............... | A61K 9/2095 514/649 |
| 2004/0005360 A1* | 1/2004 | Wang | ............... | A61K 9/00 424/473 |
| 2004/0091911 A1* | 5/2004 | Morgan | ............... | C12N 15/52 435/6.12 |
| 2004/0217186 A1* | 11/2004 | Sachs | ............... | B33Y 30/00 239/11 |
| 2006/0018942 A1* | 1/2006 | Rowe | ............... | A61L 27/54 424/422 |
| 2008/0161493 A1* | 7/2008 | Ghyzel | ............... | C09D 7/65 525/418 |
| 2008/0193665 A1* | 8/2008 | Oyanagi | ............... | C09D 11/101 522/39 |
| 2010/0015408 A1* | 1/2010 | Fong | ............... | B33Y 70/00 428/195.1 |
| 2014/0099351 A1* | 4/2014 | Adams | ............... | B33Y 10/00 264/401 |
| 2015/0290329 A1* | 10/2015 | Heilshorn | ............... | A61K 47/42 435/397 |
| 2015/0343673 A1* | 12/2015 | Williams | ............... | B29C 64/112 264/1.37 |
| 2015/0375340 A1* | 12/2015 | Cui | ............... | B29C 64/153 428/221 |
| 2016/0256610 A1* | 9/2016 | Zhou | ............... | B33Y 80/00 |
| 2016/0368077 A1* | 12/2016 | Swaminathan | ...... | B23K 10/003 |
| 2017/0087765 A1* | 3/2017 | Rundlett | ............... | B33Y 70/00 |
| 2017/0106586 A1* | 4/2017 | Keoshkerian | ............ | C09D 4/00 |
| 2017/0120530 A1* | 5/2017 | DeMuth | ............. | B23K 15/0006 |
| 2017/0203504 A1* | 7/2017 | Johnson | ............... | B29C 64/112 |
| 2017/0322487 A1* | 11/2017 | Baur | ............... | B33Y 10/00 |
| 2017/0343912 A1* | 11/2017 | Kojima | ............... | B22F 12/90 |
| 2017/0360534 A1* | 12/2017 | Sun | ............... | A61K 6/884 |
| 2018/0193922 A1* | 7/2018 | Bell | ............... | B22F 10/50 |
| 2018/0194076 A1* | 7/2018 | Bell | ............... | B29C 64/393 |
| 2018/0236549 A1* | 8/2018 | Spears | ............... | B22F 12/90 |
| 2018/0243982 A1 | 8/2018 | Shanjani et al. | | |
| 2018/0326655 A1* | 11/2018 | Herzog | ............... | B22F 10/364 |
| 2018/0368255 A1* | 12/2018 | Shih | ............... | B29C 48/0018 |
| 2019/0015320 A1* | 1/2019 | Morales | ......... | C12Y 301/27005 |
| 2019/0248932 A1* | 1/2019 | Korshikov | ............. | F23N 5/242 |
| 2019/0039310 A1* | 2/2019 | Busbee | ............... | A43B 13/026 |
| 2019/0125662 A1* | 5/2019 | Doshi | ............... | A61L 31/145 |
| 2019/0194123 A1* | 6/2019 | Das | ............... | C07C 233/46 |
| 2021/0346285 A1* | 11/2021 | Doshi | ............... | B33Y 80/00 |

FOREIGN PATENT DOCUMENTS

| | | | | |
|---|---|---|---|---|
| CN | 107428078 A | * | 12/2017 | ............. B22F 10/20 |
| DE | 102012208615 A1 | | 11/2013 | |
| DE | 102013021961 A1 | | 7/2015 | |
| EP | 1103368 A1 | | 5/2001 | |
| EP | 2532349 A1 | | 12/2012 | |
| JP | 2015143032 A | | 8/2015 | |
| JP | 2016196104 A | | 11/2016 | |
| WO | WO2009139395 A1 | | 11/2009 | |
| WO | WO2013182913 A2 | | 12/2013 | |
| WO | WO-2016019078 A1 | * | 2/2016 | ............. A61B 17/11 |
| WO | WO2017/040156 A1 | | 3/2017 | |
| WO | WO-2017077508 A1 | * | 5/2017 | ........... B29C 64/118 |

OTHER PUBLICATIONS

CN-107428078-A translation (Year: 2023).*
International Search Report dated Jul. 15, 2019 in corresponding application PCT/EP2019/057734.
Konta A.A et al: "Personalized 3D Printed Medicines: Which Techniques and Polymers Are More Successful?" Bioengineering 2017,4, 79; doi: 10.3390/bioengineering4040079, pp. 1-16.

* cited by examiner

METHOD FOR PRODUCING 3D-PRINTED ACTIVE SUBSTANCE-RELEASING SYSTEMS WITH ACTIVE SUBSTANCE DEPOTS

This nonprovisional application is a continuation of International Application No. PCT/EP2019/057734, which was filed on Mar. 27, 2019, and which claims priority to German Patent Application No. 10 2018 107 585.5, which was filed in Germany on Mar. 29, 2018, and which are both herein incorporated by reference.

BACKGROUND OF THE INVENTION

Field of the Invention

The present invention relates to a device for producing 3D-printed active substance-releasing systems and to a method for producing 3D-printed active substance-releasing systems.

The invention is related to the fields of additive manufacturing processes or molding processes for active substance-releasing medical devices, implant technology, biomaterials and combination products.

Description of the Background Art

In the prior art, active substance releasing systems (drug delivery systems) are known. The drug delivery in these takes places via the outer surface of a base body or via a two-dimensional coating—the active substance is carried by a so-called carrier. The carrier is usually a polymer. However, there are also methods in which the carrier is an implant, to the surface of which an active substance is applied. The maximum charging and concentration of the active substance are limited in terms of solubility in the polymeric active substance carrier and its coating integrity. Often, release takes place here by diffusion and is defined by the properties of the active substance-carrying polymer and the active substance itself. As a consequence, locally, medically relevant dosages can be released only for a short time.

In the documents WO2013182913A1 and EP1103368A1 (which corresponds to U.S. Pat. No. 6,821,473), stereolithographic methods for printing pharmaceutical products are known. In comparison to powder bed-based or extrusion based methods, these are more precise and make it possible to specifically adjust the degradation kinetics. The disclosed stereolithographic methods work with a focused radiation source, such as a laser. For this technique, a photo polymer bath in a trough is used, a focused light source such as a laser selectively cures the photo polymer with a certain penetration depth, then a doctor blade spreads a new layer of photo polymer which is again cured part-specific by the focused light source. This is repeated layer by layer until the component is finished. Due to the precision of the light beam source, the polymerization of the material can be precisely set. In addition, the method has the necessary accuracy to produce the smallest reservoir geometries. The document DE102013021961A1 also discloses a stereolithographic method with more than one independent beam source. Such methods create the layer application of the (initially liquid) photo polymer from a liquid bath, wherein the flow properties of the photo polymer are used, as well as doctor blades or rollers.

Also known in the prior art are the 3D printing methods polyjet printing (PJ) or multijet printing (MJM), which are based on photo polymerization and which use drop-generating printheads for material application, such as inkjet printheads. Initially and mainly used in color and photo printing applications, this technology is also used for a variety of pharmaceutical and medical tasks. The use of inkjet technology is well established in 3D printing. This applies in particular to powder-based 3D printing as well as PJ and MJM methods. In the latter methods, photo polymers are applied in a locationally selective manner in multiple layers by inkjet printheads and cured layer for layer using photo polymerization. The processing of multiple materials simultaneously is possible; it is usual to simultaneously process at least two materials: structural material and support material. The exposure for photo polymerization is carried out by using a suitable radiation source. The documents JP002016196104A, JP002016196104A and CN000205818475U disclose movable inkjet printheads and a radiation source for a photo polymerization. However, the printheads only fulfill the function of applying the structural material, which is a pure photo polymer. Simultaneous processing of a functional active substance is not disclosed.

However, the document JP002015143032A discloses a method which does not exclusively use inkjet printheads for processing photo polymers. In this method, after the photo polymers have cured using laser light sources, dye is applied to the cured material layers using an inkjet printhead. Here, however, the dye is applied to cured layers. This is done to the entire cured layer and not to specific reservoir structures. In addition, it is not described that the dye is functionally linked to the base body by targeted photo polymerization. A specific release of the dye is also not described.

The use of active substance reservoirs on implant surfaces, including a charging process by drop generation using inkjet methods, is disclosed in document DE102012208615A1. The manufacture of the reservoirs and the charging of the active substance are separate processes that must take place one after the other. For example, the reservoirs are laser-drilled in the first step. After cleaning and post-treatment, the second step is the charging of the active substance by drop generators. A production process for the manufacture of highly precise, complex components with locationally selective active substance-charged reservoirs which are built into the component directly during a contiguous manufacturing process and also have a targeted crosslinking of the active substances with the base polymer of the component is not described.

In the publication by Konta, A. A. et al., "Personalised 3D Printed Medicines: Which Techniques and Polymers Are More Successful?" (Bioengineering 2017, 4, 79; doi: 10.3390/bioengineering4040079, p. 1-16), an overview is given of the current techniques for 3D printing of drugs and their advantages and disadvantages as well as the standards for polymers and drugs that are required for successful printing. The main application of these techniques is also discussed. Additive manufacturing or 3D printing consists of a wide range of techniques, which are divided into many categories, but only three of them are used mainly for 3D printing of drugs: printing-based inkjet systems, nozzle-based deposition systems and laser-based writing systems. There are several drawbacks when using the named techniques and also, the polymers available do not always possess the optimal properties for each drug.

The prior art does not offer a high-resolution 3D printing process with which active substance-releasing systems can be produced in a cohesive process, said systems having locationally selective active substance depots with a controlled coupling that is gentle on the active substances.

SUMMARY OF THE INVENTION

It is therefore an object of the present invention to provide a device which resolves the disadvantages of the prior art and enables the construction of high-resolution active substance-releasing systems of any form with locationally selective active substance depots. The object of the invention is also to provide a method which eliminates the disadvantages of the prior art and allows for the construction of high-resolution active substance-releasing systems of any form with locationally selective active substance depots.

The exemplary device for producing a 3D-printed active substance-releasing system with active substance depots can have at least one inkjet printhead and at least one radiation source. The device also has a trough for receiving the base material that is to be processed. The base material can be a monomer, but also a polymer or a mixture of monomer and polymer. The use of several different monomers or polymers is also conceivable. Examples of these are commercially available polyethylene glycols, poly(ethylene glycol) diacrylates, and gelatin methacrylate.

Furthermore, the device includes a construction platform. The construction platform is arranged inside the trough in such a way that it is supported such that it can move in the vertical direction.

The at least one radiation source is designed in such a way that in operation it causes a polymerization of a layer of the base material on the construction platform.

According to the invention, the at least one inkjet printhead is designed in such a way that in operation it incorporates an active substance mixture, which has at least one active substance, into the base material in a locationally selective manner.

It is conceivable for the device to have further inkjet printheads, wherein each inkjet printhead can incorporate an active substance mixture in the base material in a locationally selective manner. The active substance mixture which an inkjet printhead incorporates in the base material in a locationally selective manner can be different from the active substance mixture of another inkjet printhead.

The at least one inkjet printhead can be arranged to be movable in the x-y-direction in a plane above the trough with the base material. Alternatively, it is conceivable that the construction platform can be moved. By being able to move the at least one inkjet printhead or the construction platform, the active substance mixture is incorporated in the base material in a locationally selective manner. In addition, it is conceivable that the inkjet printhead can be moved in a further longitudinal direction (z-direction).

The active substance mixture can have at least one monomer and/or at least one polymer. The use of multiple different monomers and/or polymers is also conceivable. Furthermore, the active substance mixture has at least one photo initiator and/or at least one curing agent, a so-called crosslinking agent. However, the use of several photo initiators and/or several crosslinking agents is also conceivable. Photo initiators are chemical compounds which decay into reactive molecules after absorption of light, which in turn cause the polymerization reaction. Crosslinking agents are monomers or polymers having at least three functionalities (e.g. more than two functional groups or more than one double bond), which can respond by means of polymerization reactions. These cause chain branching and thus crosslinking of the chain-like polymer molecules.

The base material also can have at least one photo initiator and/or at least one crosslinking agent. Equipping the base material with a crosslinking agent means that the active substance mixture does not have to include extra crosslinking agents. As a result, the polymerization of the base material causes the active substance to also be cross-linked with the base material.

The monomer of the base material and/or the active substance mixture can be a photo monomer. The polymer of the base material and/or the active substance mixture can be a photo polymer. Photo monomers or photo polymers polymerize when they are irradiated with a certain radiation intensity.

The monomer of the base material and/or the active substance mixture and/or the polymer of the base material and/or the active substance mixture can be (a) crosslinking agent (s).

The monomer of the base material and/or the mixture of active substances and/or the polymer of the base material and/or the mixture of active substances can have a defined number of photo initiators.

The at least one radiation source is designed in such a way that it causes a polymerization of the active substance mixture and/or cross-links the active substance mixture with the base material.

Instead of the at least one radiation source, which is used for polymerizing the base material as well as the active substance mixture, the device can also have a second radiation source or multiple radiation sources. Whereas the at least one radiation source polymerizes the base material, the second radiation source is formed such that it causes a polymerization of the active substance mixture and/or a crosslinking of the active substance mixture with the structural material. Other radiation sources of the device for further active substance mixtures are conceivable and advantageous when different active substance mixtures include various monomers/polymers, a varying number of photo initiators and/or different crosslinking agents. Each active substance mixture can then be polymerized and/or cross-linked by different radiation sources.

The inkjet printhead can also be heated. To this end, the inkjet printhead can include a heating device. The inkjet printhead preferably has a reservoir in which the active substance mixture is stored. Alternatively, the reservoir can also be heated by the reservoir also including a heating device. This way, an ideal temperature is provided which allows for the processing of liquids, which at room temperature are too viscous for an inkjet process to take place. Heating by means of the heating device takes place in consideration of the thermal stability of the active substance, which is introduced into the base material by the inkjet module.

In order to allow an afterflow of the active substance mixture, the reservoir is attached to the inkjet printhead in a self-draining manner in operation. Self-draining is achieved by means of natural forces, without any further forces. Natural forces are, for example, gravitational forces or capillary forces. Further forces, for example induced by pumps, are not required. For this purpose, the reservoir can be attached above the inkjet module, for example, in order to ensure that the mixture of active substances flows in due to an overpressure generated in this way. However, an arrangement next to or below the inkjet printhead is also conceivable.

The radiation source and/or the second radiation source and/or any further radiation source is preferably an optoelectronic component, such as, for example, a laser diode, a light diode, a light emitting diode, or an optical resonator, such as a laser, or a lithography device, for example, a lithography mask.

The radiation source and/or the second radiation source is/are preferably designed in such a way that the radiation intensity of this/these is adjustable. For this purpose, the device preferably has a controller for controlling the at least one radiation source and/or the second radiation source and/or each further radiation source, which is set up in such a way that different radiation characteristics are provided. By means of different radiation intensities it is achieved that different active substance mixtures and/or the base material, which cross-link at different radiation intensities, can be irradiated. The crosslinking is based on cleavable bonds, for example bonds that can be cleaved by hydrolysis, whereby the cleavage of the bonds and thus the release of active substances can be controlled.

The radiation source and each further radiation source are preferably designed in such a way that they generate mutually different wavelengths for the polymerization of the base material and/or of different active substance mixtures. The fact that the radiation sources generate different wavelengths makes it possible for different polymers or monomers to be used for the base material as well as for the active substance mixture. This in turn brings about a controlled polymerization, which leads to a targeted release of the active substance.

The object is also achieved by a method for producing a 3D-printed active substance-releasing system with active substance depots. The method can have the following method steps according to the invention, the method steps not having to be carried out in the order shown:

Providing a trough in which a base material and a construction platform are arranged, wherein the base material is a monomer and/or polymer. Examples of this are commercially available polyethylene glycols, poly(ethylene glycol) diacrylates and gelatin methacrylates.

Polymerizing selected regions of a layer of the base material on the construction platform. The selected regions of the layer of the base material can be polymerized by means of a radiation source on the construction platform, wherein the construction platform is arranged within the trough in such a way that the construction platform is supported so that it can be moved in the vertical direction within the trough. Other types of movable support of the construction platform are also conceivable.

Lowering the construction platform, wherein surrounding base material which is not polymerized flows in.

Smoothing the base material which has flowed in, wherein the base material is actively smoothed, for example using a doctor blade. However, other active smoothing devices are also conceivable. Another possibility of smoothing is passive smoothing, for example by waiting until the non-polymerized base material has flowed in completely and a smooth surface has formed. Active smoothing by means of a smoothing apparatus, however, has the advantage that a thickness of the layer which is polymerized can be better controlled.

At least one active substance mixture, which includes at least one active substance, is incorporated/introduced into the base material and/or the polymerized base material in a locationally selective manner by means of at least one inkjet printing process, so as to in this way generate active substance depots in the active substance-releasing system.

By lowering the construction platform, further areas of a further layer of the base material can be polymerized. This way, a three-dimensional body is built layer by layer.

Due to the layered structure of the three-dimensional body and the locationally selective introduction of the active substance mixture into the layers and/or the base material, an active substance-releasing system is provided with active substance depots at specific localized positions of the active substance-releasing system.

The use of multiple inkjet printheads in the inkjet printing method is preferred for incorporating various active substance mixtures having different characteristics into the base material.

At least one inkjet printhead is preferably arranged in a plane above the trough with the base material so as to be movable in the x-y-direction. Alternatively, it is conceivable that the construction platform can be moved. The displaceability of the at least one inkjet printhead or the displaceability of the construction platform ensures that the active substance mixture is incorporated into the base material in a locationally selective manner. In addition, it is conceivable that the inkjet printhead can be moved in a further longitudinal direction (z-direction).

The active substance mixture has, for example, at least one monomer and/or at least one polymer. Furthermore, the active substance mixture can preferably have at least one photo initiator and/or at least one crosslinking agent. Photo initiators are chemical compounds that break down into reactive molecules after absorption of light, which molecules in turn trigger the polymerization reaction. Crosslinking agents are monomers or polymers having at least three functionalities (more than two functional groups or more than one double bond), which can respond by means of polymerization reactions. The latter cause a chain branching and thus a network of chain-like polymer molecules.

In an alternative embodiment, the base material can have, only or also, at least one photo initiator and/or at least one crosslinking agent. Equipping the base material with a crosslinking agent means that the active substance mixture does not need additional crosslinking agents. By polymerizing the base material, the active substance is cross-linked with the base material.

The monomer of the base material and/or of the active substance mixture is preferably a photo monomer. The polymer of the base material and/or of the active substance mixture is preferably a photo polymer. Photo monomers or photo polymers polymerize when they are irradiated with a certain radiation intensity.

The monomer of the base material and/or of the active substance mixture is preferably a crosslinking agent. Alternatively or additionally, the polymer of the base material and/or of the active substance mixture is/are a crosslinking agent/crosslinking agents. Forming the base material as a crosslinking agent means that the active substance mixture does not have to have additional crosslinking agents. By polymerizing the base material, the active substance is cross-linked with the base material.

The monomer of the base material and/or of the active substance mixture and/or the polymer of the base material and/or of the active substance mixture can also have a defined number of photo initiators.

After the application of the active substance mixture, the radiation source causes a polymerization of the active substance mixture and/or a crosslinking of the active substance mixture with the base material. A further radiation source can also be used for this, wherein the first radiation source polymerizes the base material and the further radiation source polymerizes the active substance mixture. Polymerization also preferably leads to crosslinking of the base material with the active substance.

Preferably, the inkjet printhead heats the active substance mixture. The active substance mixture can be in a reservoir attached to the inkjet printhead. It is also conceivable that the reservoir is heated in order to provide a flowable liquid.

Furthermore, a reservoir is attached to the inkjet printhead in such a way that the active substance mixture afterflows. For this purpose, for example, the reservoir can be attached above the inkjet printhead. By means of this arrangement, an overpressure is generated with which the afterflow is ensured. The reservoir can, however, also be attached next to or below the inkjet printhead; other positions on the inkjet printhead are also conceivable.

The radiation intensity of the first radiation source and/or the further radiation source can preferably be adjusted. Using different radiation intensities can achieve crosslinking of different active substance mixtures and/or the base material at different radiation intensities. The crosslinking is based on cleavable bonds, for example hydrolytically cleavable bonds, whereby the cleavage of the bonds and thus the active substance release can be controlled. The radiation intensity of the first and/or the further radiation source is preferably adjustable by means of a controller which controls the first and/or the further radiation source.

The first radiation source and the further radiation source are preferably designed such that they generate mutually different wavelengths with which they irradiate the polymers and/or monomers of the base material and/or the at least one active substance mixture. Each monomer or polymer polymerizes at different wavelengths. The fact that the radiation sources generate different wavelengths means that different polymers or monomers can be used for the base material as well as for the active substance mixture or the active substance mixtures. This in turn brings about a controlled polymerization, which leads to a targeted release of the active substance.

Examples of polymers which can be used in the device or in the method are commercially available polyethylene glycols, poly(ethylene glycol) diacrylate and gelatin methacrylate. Other polymers are conceivable for use in the device or in the method.

Examples of photo initiators which are used in the method according to the invention or in the device are 2-hydroxy-4'-(2-hydroxyethoxy)-2-methylpropiophenone or lithium-phenyl-2,4,6-trimethylbenzoylphosphinate (LAP).

The active substance mixture or the active substance mixtures which are used in the device or in the method can comprise further constituents, for example solvents, prodrugs and/or additives, which increase the stability of the active substance mixture.

Active substances in the device and/or in the method are preferably pharmaceutical drugs. However, proteins, toxins or substances which are employed for analytical tasks can also be used. Other types of substances are conceivable.

The inventive device and the inventive method have several advantages as compared to the prior art.

The invention provides a device which eliminates the disadvantages of the prior art and allows for the construction of high-resolution active substance-releasing systems of any form with locationally selective active substance depots. The invention also provides a method which eliminates the disadvantages of the prior art and allows for the construction of high-resolution active substance-releasing systems of any form with locationally selective active substance depots.

The active substance or substances can be incorporated in the depots in different ways. The active substances can be incorporated into the basic structure of the active substance-releasing system without being cross-linked or they can also be connected to the basic structure with different degrees of crosslinking and covalent bonds, whereby targeted release kinetics can be achieved. The local selectivity and the number of cross-links or bonds create targeted diffusion paths for the active substance. Together with the individual degradation kinetics, the release of the active substances is controlled. In this way, long release periods of 6 to 12 months can be achieved, but also longer or significantly shorter release periods can be set. This targeted drug release/controlled release of active substances is made possible by various degrees of crosslinking and/or targeted controlled crosslinking.

Depending on the composition of the photo polymer (for example, number of photo initiators), different radiation sources or different radiation intensities of a source are suitable for crosslinking the active substance with the base polymer. The simultaneous or staggered use of multiple radiation sources as well as the use of different radiation intensities of a radiation source can be used to control the polymerization and crosslinking of the active substance with the base material. Multiple radiation sources can be operated with the same or with different wavelengths. In this context, different photo initiators tailored to the respective wavelengths can be components of the photo polymer. In this context, the newly developed method allows for inkjet printheads and radiation sources to work in a simultaneous or staggered manner.

The method allows for a high-resolution structure. It is possible to produce basic structures which can be charged by the inkjet printhead during the construction process with an active substance or an active substance polymer mixture. In the newly developed process, the active substance or the active substance mixture can be specifically incorporated in the base material. This takes place via a controlled photo polymerization. One or more active substances can be specifically cross-linked with the basic structure of the base polymer by using different crosslinking agents in the active substance mixture. However, the active substance can also be incorporated in the basic structure of the base polymer without being cross-linked. In this way, the active substance release of the active substance-releasing system can be adjusted in a targeted manner.

Several different radiation sources can operate simultaneously or in a staggered manner. The intensity of a radiation source is adjustable. The energy input for the polymerization can thus be adjusted. The composition of the photo polymer mixtures can also be varied to control the polymerization. For example, the specification and number of crosslinking agents and photo initiators used can be changed. For example, depending on the photo initiator, different radiation intensities for crosslinking the active substance with the base material are suitable.

After the construction process, the active substance-releasing system produced with the method can be cleaned with the help of suitable washing solutions and, if necessary, be secondarily cross-linked in a post-processing step by means of a radiation source using two-dimensional radiation.

The active substance-releasing system produced with the method can be of any form and the active substance depots can be introduced in a locationally selective manner and in any number. This allows for the diffusion paths of the active substance to be formed. The release of the active substances is controlled together with the individual degradation kinetics of the covalent bonds and the degree of crosslinking. In addition, the method characterizes low heat input, resulting in gentle processing of the active substances.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
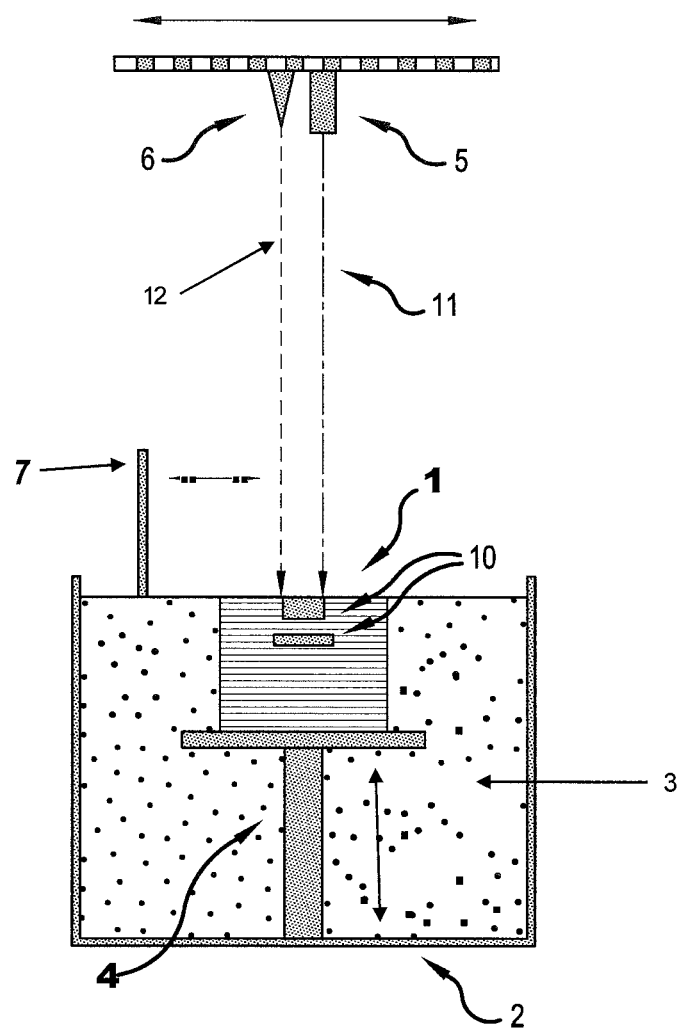
FIG. 1 shows a device according to an exemplary embodiment.

FIG. 1 shows a device for producing a 3D-printed active substance-releasing system 1 with active substance depots 10. As shown in FIG. 1, the device has at least one inkjet printhead 6 and at least one radiation source 5. Furthermore, the device has a trough 2 for receiving the base material 3 to be processed, wherein the base material 3 is a monomer and/or a polymer. A construction platform 4 is arranged inside the trough in such a way that the construction platform 4 is mounted so as to be movable in the vertical direction. The at least one radiation source 5 is designed in such a way that it emits a beam 11 onto the base material which, in a locationally selective manner, causes a polymerization of selected regions of a layer of the base material 3 on the construction platform 4. According to the invention, the at least one inkjet printhead 6 is designed in such a way that it incorporates/introduces an active substance mixture into the base material 3 in a locationally selective manner by means of a dosed jet 12. The active substance mixture has at least one active substance.

FIG. 1 shows a device with which the inventive method for producing a 3D printed active substance-releasing system with active substance depots 10 can be performed. The method has the following method steps:

Filling a trough 2 with a base material 3, wherein the base material 3 is a monomer and/or polymer, Polymerizing selected regions of a layer of the base material 3 by means of a radiation source 5 on a construction platform 4, wherein the construction platform 4 is arranged within the trough 2 in such a way that the construction platform 4 is supported within the trough 2 so as to be movable in the vertical direction (direction of the arrow shown), Introduction of an active substance mixture by means of a dosed jet, which has at least one active substance, by means of an inkjet printing process. To this end, an inkjet printhead 6 is used which incorporates the active substance mixture in a locationally selective manner in the base material 3 and/or in the polymerized layer of the base material.

Lowering the construction platform 4, wherein base material 3 surrounding the construction platform, which is not polymerized, flows in, By lowering the construction platform, further selected regions of a further layer can be polymerized. As a result, a layered structure of a three-dimensional body forming the basic structure of the active substance-releasing system is possible. By introducing the active substance mixture into selected regions of the three-dimensional body, active substance depots 10 are provided.

After lowering the construction platform, the base material 3 surrounding the construction platform flows in. Said base material can be smoothed in one method step.

In an embodiment of the method, after applying the active substance mixture, the radiation source 5 and/or a second and/or other sources of radiation sources causes/cause the polymerization of the active substance mixture and/or a crosslinking of the active substance mixture with the base material.

In addition to the method steps described, in a further embodiment, the inkjet printhead heats the active substance mixture.

FIG. 1 additionally displays a doctor blade 7. This embodiment of the device allows for the base material 3 to be smoothed.

Figure 2:
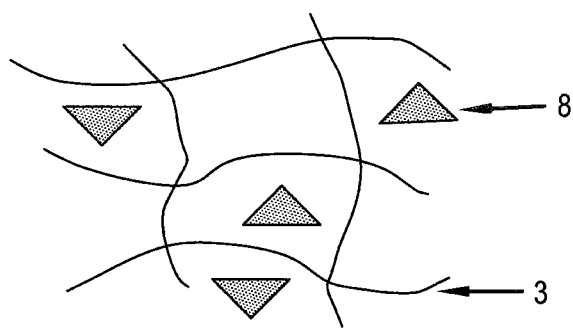
FIG. 2 shows an active substance-releasing system.

FIG. 2 displays an active substance-releasing system 1, produced according to the method according to the invention and/or with a device according to the invention. FIG. 2 shows a non-cross-linked active substance-releasing system 1. An active substance 8 is incorporated into a base material 3.

Figure 3:
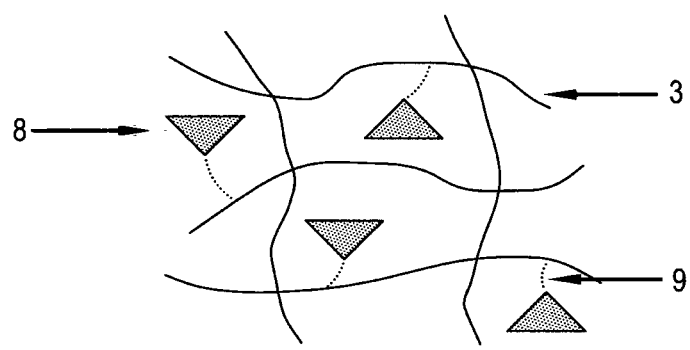
FIG. 3 shows an active substance-releasing system with crosslinking agent.

FIG. 3 shows an active substance-releasing system 1, produced according to the method according to the invention and/or with a device according to the invention. FIG. 3 shows a cross-linked active substance-releasing system 1. An active substance 8 is incorporated in a base material 3. The active substance 8 is cross-linked with base material 3. This is achieved by crosslinking agents which are present in the active substance mixture and/or the base material 3. By means of a radiation source 5 and a radiation intensity, the crosslinking agents are activated. By varying the radiation intensity and the choice of the crosslinking agent and its concentration, different degrees of crosslinking can be achieved. These cause a targeted release of the active substance in the active substance-releasing system.

In all embodiments, the active substance mixture and/or the base material may be configured as follows:

The active substance mixture can comprise a monomer and/or a polymer. In addition, the active substance mixture can have a photo initiator and/or a crosslinking agent. This allows for the active substance mixture to polymerize, which in turn leads to an increased stability of the active substance mixture, a crosslinking of the active substance mixture with the base material and a varying diffusion of the active substance.

Also the base material 3 or only the base material 3 can have at least one photo initiator and/or at least one crosslinking agent.

The monomer of the base material and/or the active substance mixture can be configured as a photo monomer and/or the polymer of the base material and/or the active substance mixture can be configured as a photo polymer.

The monomer of the base material and/or the active substance mixture and/or the polymer of the base material and/or the active substance mixture can be configured as a crosslinking agent.

The monomer of the base material and/or of the active substance mixture and/or the polymer of the base material and/or of the active substance mixture can also have a defined number of photo initiators.

In all embodiments, the radiation source 5 and/or a further radiation source may be configured as follows:

The first radiation source 5 is designed in FIG. 1 in such a way that it causes a polymerization of the active substance mixture in operation. Alternatively or additionally, the radiation source 5 brings about a crosslinking of the active substance mixture with the base material 3.

In a further embodiment, a second radiation source is arranged (not shown here). When in use, this brings about a polymerization of the active substance mixture and/or a crosslinking of the active substance mixture with the base material 3.

The radiation source 5 is designed as a laser, a laser diode, a light diode or a lithography. The second radiation source can also be designed as a laser, a laser diode, a light diode or a lithography. In order to achieve different radiation intensities and wavelengths between different radiation sources, the second radiation source can be designed differently from the first radiation source. For example, the radiation source 5 can be a laser diode and the second radiation source a lithography. Other combinations are possible.

In an embodiment, the radiation source 5 and/or the second radiation source is/are designed in such a way that its/their radiation intensity is adjustable.

In an embodiment, the radiation source 5 and the second radiation source are configured to generate mutually different wavelengths.

In all embodiments, the inkjet printhead 6 can be designed as follows:

In an embodiment, the inkjet printhead 6 can be heated. To this end, it includes a heating device.

In an embodiment, the inkjet printhead 6 comprises a reservoir (not shown here) for receiving the active substance mixture. The reservoir can be designed to be heatable. For this purpose, the reservoir has a heating device.

To ensure that the active substance mixture continues to flow in, the reservoir can be attached to the inkjet printhead 6 in such a way that only natural forces, i.e. no additional forces, for example forces generated by a pump, are required to achieve an afterflow of the active substance mixture. Natural forces can be, for example, gravitational forces or capillary forces.

Since the device described in detail above and the method are exemplary embodiments, these can be modified in the customary manner by the person skilled in the art to a large extent without departing from the scope of the invention. In particular, the specific embodiments of the device can also be presented in some other form than the one described herein. Likewise, the device can be designed in some other form if this is necessary due to lack of space. Further, the use of the undefined article "a" does not exclude that the features in question can be present in multiple instances.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A hybrid additive method for producing a 3D-printed active substance-releasing system, the method comprising:
   sequentially building layers of the 3D-printed active substance-releasing system utilizing:
      an inkjet printhead for performing an inkjet printing process, and
      a first radiation source with a trough for receiving a base material to be processed and a construction platform in the trough for carrying out a stereolithography process, wherein the base material is a monomer and/or a polymer
   the layers being sequentially built by:
      polymerizing selected regions of a first layer of the base material that is on the construction platform using the first radiation source to form a polymerized base material at the selected regions; and
      spatially selectively incorporating at least one active substance mixture via the at least one inkjet printhead, before and/or after forming the polymerized base material, into the base material and/or into the polymerized base material and/or into an area within the first layer via the inkjet printing process and polymerizing the at least one active substance mixture using the first radiation source to form at least one layer, so that the at least one layer comprises both the polymerized base material and the at least one active substance mixture that has been polymerized, with the polymerized base material and the at least one active substance mixture that has been polymerized being locally separated from each other,
   wherein the at least one active substance mixture comprises a monomer and/or a polymer and at least one active substance, and wherein the base material is devoid of the at least one active substance until the spatially selective incorporation of the at least one active substance mixture via the inkjet printing process, and
   wherein the at least one active substance is a pharmaceutical drug, a protein, a toxin or a substance used for analytical tasks.

2. The method according to claim 1, wherein the at least one active substance mixture also has a photo initiator and/or a crosslinking agent.

3. The method according to claim 1, wherein the base material also has a photo initiator and/or a crosslinking agent.

4. The method according to claim 1, wherein the monomer of the base material and/or the monomer of the at least one active substance mixture is a photo monomer and/or the polymer of the base material and/or the polymer of the at least one active substance mixture is a photo polymer.

5. The method according to claim 1, wherein the monomer of the base material and/or the monomer of the at least one active substance mixture and/or the polymer of the base material and/or the polymer of the at least one active substance mixture is/are a crosslinking agent/crosslinking agents.

6. The method according to claim 1, wherein the monomer of the base material and/or the monomer of the at least one active substance mixture and/or the polymer of the base material and/or the polymer of the at least one active substance mixture has/have a defined number of photo initiators.

7. The method according to claim 1, wherein after incorporating the at least one active substance mixture, the polymerization of the at least one active substance mixture and/or a crosslinking of the at least one active substance mixture with the base material is caused by different light exposure parameters using the first radiation source or a further radiation source, so that the at least one active substance mixture is fixed at the specific position.

8. The method according to claim 7, wherein one of the light exposure parameters is radiation intensity, wherein the radiation intensity of the first radiation source and/or of the further radiation source is set, and wherein the radiation intensity of the first radiation source is different from the radiation intensity of the further radiation source.

9. The method according to claim 7, wherein one of the light exposure parameters is wavelength, and wherein the first radiation source and the further radiation source generate mutually different wavelengths.

10. The method according to claim 1, wherein the at least one active substance mixture is heated.

11. The method according to claim 1, wherein a reservoir is mounted on the at least one inkjet printhead such that an afterflow of the at least one active substance mixture is achieved.

12. The method according to claim 1, wherein after incorporating the at least one active substance mixture, the construction platform having the polymerized base material thereon is lowered, and wherein by lowering the construction platform with the polymerized base material thereon, a spacing is created in which the base material surrounding the construction platform, that was not previously polymerized, flows into the spacing to then be polymerized by the first radiation source.

13. The method according to claim 12, wherein after the base material surrounding the construction platform flows into the spacing created by the lowering of the construction platform, the base material is smoothed before being polymerized.

* * * * *